(12) United States Patent
Mazza et al.

(10) Patent No.: US 8,029,441 B2
(45) Date of Patent: Oct. 4, 2011

(54) ANALYTE SENSOR TRANSMITTER UNIT CONFIGURATION FOR A DATA MONITORING AND MANAGEMENT SYSTEM

(75) Inventors: John C. Mazza, Pleasanton, CA (US); Andrew H. Naegeli, Walnut Creek, CA (US); Gary Ashley Stafford, Hayward, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 542 days.

(21) Appl. No.: 11/365,334

(22) Filed: Feb. 28, 2006

(65) Prior Publication Data
US 2009/0102678 A1 Apr. 23, 2009

(51) Int. Cl.
*A61B 5/00* (2006.01)
*A61B 5/05* (2006.01)

(52) U.S. Cl. ........ 600/309; 600/300; 600/345; 600/347; 600/365

(58) Field of Classification Search .................. 600/365, 600/345, 347
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,305,401 A * | 12/1981 | Reissmueller et al. ....... 600/503 |
| 4,327,725 A | 5/1982 | Cortese et al. |
| 4,344,438 A | 8/1982 | Schultz |
| 4,349,728 A | 9/1982 | Phillips et al. |
| 4,425,920 A | 1/1984 | Bourland et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,703,756 A | 11/1987 | Gough et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |

(Continued)

FOREIGN PATENT DOCUMENTS
DE 4401400 7/1995
(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Patricia Mallari
(74) *Attorney, Agent, or Firm* — Jackson & Co., LLP

(57) ABSTRACT

Method and system for providing analyte sensor alignment and retention mechanism for improved connectivity with a transmitter unit for electrical connection, and further including transmitter unit contact pins with metal components to improve electrical conductivity with the analyte sensor in an analyte monitoring and management system is provided.

20 Claims, 10 Drawing Sheets

U.S. PATENT DOCUMENTS

| | | | |
|---|---|---|---|
| 4,854,322 A | 8/1989 | Ash et al. | |
| 4,890,620 A | 1/1990 | Gough | |
| 4,925,268 A | 5/1990 | Iyer et al. | |
| 4,953,552 A | 9/1990 | DeMarzo | |
| 4,986,271 A | 1/1991 | Wilkins | |
| 4,995,402 A | 2/1991 | Smith et al. | |
| 5,000,180 A | 3/1991 | Kuypers et al. | |
| 5,002,054 A | 3/1991 | Ash et al. | |
| 5,019,974 A | 5/1991 | Beckers | |
| 5,050,612 A | 9/1991 | Matsumura | |
| 5,055,171 A | 10/1991 | Peck | |
| 5,068,536 A | 11/1991 | Rosenthal | |
| 5,082,550 A | 1/1992 | Rishpon et al. | |
| 5,106,365 A | 4/1992 | Hernandez | |
| 5,122,925 A | 6/1992 | Inpyn | |
| 5,165,407 A | 11/1992 | Wilson et al. | |
| 5,202,261 A * | 4/1993 | Musho et al. | 204/403.09 |
| 5,205,297 A * | 4/1993 | Montecalvo et al. | 607/152 |
| 5,246,867 A | 9/1993 | Lakowicz et al. | |
| 5,262,035 A | 11/1993 | Gregg et al. | |
| 5,262,305 A | 11/1993 | Heller et al. | |
| 5,264,104 A | 11/1993 | Gregg et al. | |
| 5,264,105 A | 11/1993 | Gregg et al. | |
| 5,279,294 A | 1/1994 | Anderson et al. | |
| 5,285,792 A | 2/1994 | Sjoquist et al. | |
| 5,293,877 A | 3/1994 | O'Hara et al. | |
| 5,299,571 A | 4/1994 | Mastrototaro | |
| 5,320,725 A | 6/1994 | Gregg et al. | |
| 5,322,063 A | 6/1994 | Allen et al. | |
| 5,340,722 A | 8/1994 | Wolfbeis et al. | |
| 5,342,789 A | 8/1994 | Chick et al. | |
| 5,356,786 A | 10/1994 | Heller et al. | |
| 5,360,404 A | 11/1994 | Novacek et al. | |
| 5,372,427 A | 12/1994 | Padovani et al. | |
| 5,379,238 A | 1/1995 | Stark | |
| 5,390,671 A | 2/1995 | Lord et al. | |
| 5,391,250 A | 2/1995 | Cheney, II et al. | |
| 5,408,999 A | 4/1995 | Singh et al. | |
| 5,411,647 A | 5/1995 | Johnson et al. | |
| 5,425,868 A | 6/1995 | Pedersen | |
| 5,431,160 A | 7/1995 | Wilkins | |
| 5,431,921 A | 7/1995 | Thombre | |
| 5,462,645 A | 10/1995 | Albery et al. | |
| 5,497,772 A | 3/1996 | Schulman et al. | |
| 5,507,288 A | 4/1996 | Bocker et al. | |
| 5,509,410 A | 4/1996 | Hill et al. | |
| 5,514,718 A | 5/1996 | Lewis et al. | |
| 5,531,878 A | 7/1996 | Vadgama et al. | |
| 5,568,806 A | 10/1996 | Cheney, II et al. | |
| 5,569,186 A | 10/1996 | Lord et al. | |
| 5,582,184 A | 12/1996 | Erickson et al. | |
| 5,586,553 A | 12/1996 | Halili et al. | |
| 5,593,852 A | 1/1997 | Heller et al. | |
| 5,609,575 A | 3/1997 | Larson et al. | |
| 5,628,310 A | 5/1997 | Rao et al. | |
| 5,653,239 A | 8/1997 | Pompei et al. | |
| 5,665,222 A | 9/1997 | Heller et al. | |
| 5,711,001 A | 1/1998 | Bussan et al. | |
| 5,711,861 A | 1/1998 | Ward et al. | |
| 5,772,586 A | 6/1998 | Heinonen et al. | |
| 5,791,344 A | 8/1998 | Schulman et al. | |
| 5,800,420 A * | 9/1998 | Gross et al. | 604/890.1 |
| 5,899,855 A | 5/1999 | Brown | |
| 5,925,021 A | 7/1999 | Castellano et al. | |
| 5,935,224 A | 8/1999 | Svancarek et al. | |
| 5,942,979 A | 8/1999 | Luppino | |
| 5,954,643 A * | 9/1999 | VanAntwerp et al. | 600/316 |
| 5,957,854 A | 9/1999 | Besson et al. | |
| 5,964,993 A | 10/1999 | Blubaugh, Jr. et al. | |
| 5,965,380 A | 10/1999 | Heller et al. | |
| 5,971,922 A | 10/1999 | Arita et al. | |
| 5,995,860 A | 11/1999 | Sun et al. | |
| 6,001,067 A | 12/1999 | Shults et al. | |
| 6,024,699 A | 2/2000 | Surwit et al. | |
| 6,049,727 A | 4/2000 | Crothall | |
| 6,083,710 A | 7/2000 | Heller et al. | |
| 6,088,608 A | 7/2000 | Schulman et al. | |
| 6,091,976 A | 7/2000 | Pfeiffer et al. | |
| 6,093,172 A | 7/2000 | Funderburk et al. | |
| 6,103,033 A | 8/2000 | Say et al. | |
| 6,117,290 A | 9/2000 | Say et al. | |
| 6,119,028 A | 9/2000 | Schulman et al. | |
| 6,120,676 A | 9/2000 | Heller et al. | |
| 6,121,009 A | 9/2000 | Heller et al. | |
| 6,121,611 A | 9/2000 | Lindsay et al. | |
| 6,122,351 A | 9/2000 | Schlueter, Jr. et al. | |
| 6,134,461 A | 10/2000 | Say et al. | |
| 6,162,611 A | 12/2000 | Heller et al. | |
| 6,175,752 B1 | 1/2001 | Say et al. | |
| 6,200,265 B1 | 3/2001 | Walsh et al. | |
| 6,212,416 B1 | 4/2001 | Ward et al. | |
| 6,219,574 B1 | 4/2001 | Cormier et al. | |
| 6,233,471 B1 | 5/2001 | Berner et al. | |
| 6,248,067 B1 | 6/2001 | Causey, III et al. | |
| 6,264,810 B1 * | 7/2001 | Stol et al. | 204/286.1 |
| 6,275,717 B1 * | 8/2001 | Gross et al. | 600/345 |
| 6,284,478 B1 | 9/2001 | Heller et al. | |
| 6,293,925 B1 | 9/2001 | Safabash et al. | |
| 6,295,506 B1 | 9/2001 | Heinonen et al. | |
| 6,306,104 B1 | 10/2001 | Cunningham et al. | |
| 6,309,884 B1 | 10/2001 | Cooper et al. | |
| 6,329,161 B1 | 12/2001 | Heller et al. | |
| 6,360,888 B1 | 3/2002 | McIvor et al. | |
| 6,366,794 B1 | 4/2002 | Moussy et al. | |
| 6,377,828 B1 | 4/2002 | Chaiken et al. | |
| 6,379,301 B1 | 4/2002 | Worthington et al. | |
| 6,418,332 B1 * | 7/2002 | Mastrototaro et al. | 600/316 |
| 6,424,847 B1 | 7/2002 | Mastrototaro et al. | |
| 6,427,088 B1 | 7/2002 | Bowman, IV et al. | |
| 6,440,068 B1 | 8/2002 | Brown et al. | |
| 6,478,736 B1 | 11/2002 | Mault | |
| 6,484,046 B1 | 11/2002 | Say et al. | |
| 6,514,718 B2 | 2/2003 | Heller et al. | |
| 6,522,927 B1 | 2/2003 | Bishay et al. | |
| 6,544,212 B2 | 4/2003 | Galley et al. | |
| 6,551,494 B1 | 4/2003 | Heller et al. | |
| 6,558,321 B1 | 5/2003 | Burd et al. | |
| 6,558,351 B1 | 5/2003 | Steil et al. | |
| 6,560,471 B1 | 5/2003 | Heller et al. | |
| 6,561,978 B1 | 5/2003 | Conn et al. | |
| 6,562,001 B2 | 5/2003 | Lebel et al. | |
| 6,564,105 B2 | 5/2003 | Starkweather et al. | |
| 6,565,509 B1 | 5/2003 | Say et al. | |
| 6,571,128 B2 | 5/2003 | Lebel et al. | |
| 6,576,101 B1 | 6/2003 | Heller et al. | |
| 6,577,899 B2 | 6/2003 | Lebel et al. | |
| 6,579,690 B1 | 6/2003 | Bonnecaze et al. | |
| 6,585,644 B2 | 7/2003 | Lebel et al. | |
| 6,591,125 B1 | 7/2003 | Buse et al. | |
| 6,595,919 B2 | 7/2003 | Berner et al. | |
| 6,605,200 B1 | 8/2003 | Mao et al. | |
| 6,605,201 B1 | 8/2003 | Mao et al. | |
| 6,607,509 B2 | 8/2003 | Bobroff et al. | |
| 6,610,012 B2 | 8/2003 | Mault | |
| 6,633,772 B2 | 10/2003 | Ford et al. | |
| 6,635,014 B2 | 10/2003 | Starkweather et al. | |
| 6,648,821 B2 | 11/2003 | Lebel et al. | |
| 6,654,625 B1 | 11/2003 | Say et al. | |
| 6,659,948 B2 | 12/2003 | Lebel et al. | |
| 6,668,196 B1 | 12/2003 | Villegas et al. | |
| 6,671,534 B2 * | 12/2003 | Putz | 600/378 |
| 6,687,546 B2 | 2/2004 | Lebel et al. | |
| 6,689,056 B1 | 2/2004 | Kilcoyne et al. | |
| 6,694,191 B2 | 2/2004 | Starkweather et al. | |
| 6,695,860 B1 | 2/2004 | Ward et al. | |
| 6,698,269 B2 | 3/2004 | Baber et al. | |
| 6,702,857 B2 | 3/2004 | Brauker et al. | |
| 6,733,446 B2 | 5/2004 | Lebel et al. | |
| 6,740,075 B2 | 5/2004 | Lebel et al. | |
| 6,741,877 B1 | 5/2004 | Shults et al. | |
| 6,746,582 B2 | 6/2004 | Heller et al. | |
| 6,758,810 B2 | 7/2004 | Lebel et al. | |
| 6,770,030 B1 | 8/2004 | Schaupp et al. | |
| 6,790,178 B1 | 9/2004 | Mault et al. | |
| 6,809,653 B1 | 10/2004 | Mann et al. | |
| 6,810,290 B2 | 10/2004 | Lebel et al. | |
| 6,811,533 B2 | 11/2004 | Lebel et al. | |

| Patent No. | Date | Inventor |
|---|---|---|
| 6,811,534 B2 | 11/2004 | Bowman, IV et al. |
| 6,813,519 B2 | 11/2004 | Lebel et al. |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,263 B2 | 5/2005 | Shin et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,950,708 B2 | 9/2005 | Bowman IV, et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,022,072 B2 | 4/2006 | Fox et al. |
| 7,024,245 B2 | 4/2006 | Lebel et al. |
| 7,029,444 B2 | 4/2006 | Shin et al. |
| 7,041,068 B2 | 5/2006 | Freeman et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,226,978 B2 | 6/2007 | Tapsak et al. |
| 7,267,665 B2 | 9/2007 | Steil et al. |
| 7,276,029 B2 | 10/2007 | Goode, Jr. et al. |
| 7,299,082 B2 | 11/2007 | Feldman et al. |
| 7,310,544 B2 * | 12/2007 | Brister et al. ............ 600/345 |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,402,153 B2 | 7/2008 | Steil et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,547,281 B2 | 6/2009 | Hayes et al. |
| 7,569,030 B2 | 8/2009 | Lebel et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,618,369 B2 | 11/2009 | Hayter et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 2002/0019022 A1 | 2/2002 | Dunn et al. |
| 2002/0042090 A1 | 4/2002 | Heller et al. |
| 2002/0057993 A1 * | 5/2002 | Maisey et al. ............ 422/82.01 |
| 2002/0103499 A1 | 8/2002 | Perez et al. |
| 2002/0106709 A1 | 8/2002 | Potts et al. |
| 2002/0128594 A1 | 9/2002 | Das et al. |
| 2002/0161288 A1 | 10/2002 | Shin et al. |
| 2002/0169635 A1 | 11/2002 | Shillingburg |
| 2003/0004403 A1 | 1/2003 | Drinan et al. |
| 2003/0023317 A1 | 1/2003 | Brauker et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0100821 A1 | 5/2003 | Heller et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0039298 A1 | 2/2004 | Abreu |
| 2004/0040840 A1 | 3/2004 | Mao et al. |
| 2004/0045879 A1 | 3/2004 | Shults et al. |
| 2004/0064068 A1 | 4/2004 | DeNuzzio et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0138588 A1 | 7/2004 | Saikley et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0254433 A1 | 12/2004 | Bandis et al. |
| 2004/0267300 A1 | 12/2004 | Mace |
| 2005/0004439 A1 | 1/2005 | Shin et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0031689 A1 | 2/2005 | Shults et al. |
| 2005/0038332 A1 | 2/2005 | Saidara et al. |
| 2005/0043598 A1 | 2/2005 | Goode, Jr. et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0112169 A1 | 5/2005 | Brauker et al. |
| 2005/0113653 A1 | 5/2005 | Fox et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0239154 A1 | 10/2005 | Feldman et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0287620 A1 | 12/2005 | Heller et al. |
| 2006/0001538 A1 | 1/2006 | Kraft et al. |
| 2006/0004270 A1 | 1/2006 | Bedard et al. |
| 2006/0015020 A1 | 1/2006 | Neale et al. |
| 2006/0015024 A1 | 1/2006 | Brister et al. |
| 2006/0016700 A1 | 1/2006 | Brister et al. |

| | | |
|---|---|---|
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1* | 1/2006 | Brister et al. ............... 600/345 |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0155180 A1 | 7/2006 | Brister et al. |
| 2006/0166629 A1 | 7/2006 | Reggiardo |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183985 A1 | 8/2006 | Brister et al. |
| 2006/0189863 A1 | 8/2006 | Peyser et al. |
| 2006/0222566 A1 | 10/2006 | Brauker et al. |
| 2006/0224109 A1 | 10/2006 | Steil et al. |
| 2006/0229512 A1 | 10/2006 | Petisce et al. |
| 2006/0247508 A1 | 11/2006 | Fennell |
| 2006/0272652 A1 | 12/2006 | Stocker et al. |
| 2007/0016381 A1 | 1/2007 | Kamath et al. |
| 2007/0027381 A1 | 2/2007 | Stafford |
| 2007/0033074 A1 | 2/2007 | Nitzan et al. |
| 2007/0060814 A1 | 3/2007 | Stafford |
| 2007/0066873 A1 | 3/2007 | Kamath et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0106135 A1 | 5/2007 | Sloan et al. |
| 2007/0124002 A1 | 5/2007 | Estes et al. |
| 2007/0149875 A1 | 6/2007 | Ouyang et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0235331 A1 | 10/2007 | Simpson et al. |
| 2007/0249922 A1 | 10/2007 | Peyser et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097289 A1 | 4/2008 | Steil et al. |
| 2008/0108942 A1 | 5/2008 | Brister et al. |
| 2008/0154513 A1 | 6/2008 | Kovatchev et al. |
| 2008/0167543 A1 | 7/2008 | Say et al. |
| 2008/0172205 A1 | 7/2008 | Breton et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0208113 A1 | 8/2008 | Damiano et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0262469 A1 | 10/2008 | Brister et al. |
| 2008/0275313 A1 | 11/2008 | Brister et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2009/0005665 A1 | 1/2009 | Hayter et al. |
| 2009/0006034 A1 | 1/2009 | Hayter et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0099436 A1 | 4/2009 | Brister et al. |
| 2009/0105636 A1 | 4/2009 | Hayter et al. |
| 2009/0124877 A1 | 5/2009 | Shariati et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |

| | | | |
|---|---|---|---|
| 2009/0143659 A1 | 6/2009 | Ying et al. | |
| 2009/0143660 A1 | 6/2009 | Brister et al. | |
| 2009/0156919 A1 | 6/2009 | Brister et al. | |
| 2009/0156924 A1 | 6/2009 | Shariati et al. | |
| 2009/0163790 A1 | 6/2009 | Brister et al. | |
| 2009/0163791 A1 | 6/2009 | Brister et al. | |
| 2009/0164190 A1 | 6/2009 | Hayter | |
| 2009/0164239 A1 | 6/2009 | Hayter et al. | |
| 2009/0164251 A1 | 6/2009 | Hayter | |
| 2009/0178459 A1 | 7/2009 | Li et al. | |
| 2009/0182217 A1 | 7/2009 | Li et al. | |
| 2009/0192366 A1 | 7/2009 | Mensinger et al. | |
| 2009/0192380 A1 | 7/2009 | Shariati et al. | |
| 2009/0192722 A1 | 7/2009 | Shariati et al. | |
| 2009/0192724 A1 | 7/2009 | Brauker et al. | |
| 2009/0192745 A1 | 7/2009 | Kamath et al. | |
| 2009/0192751 A1 | 7/2009 | Kamath et al. | |
| 2009/0198118 A1 | 8/2009 | Hayter et al. | |
| 2009/0203981 A1 | 8/2009 | Brauker et al. | |
| 2009/0204341 A1 | 8/2009 | Brauker et al. | |
| 2009/0216103 A1 | 8/2009 | Brister et al. | |
| 2009/0240120 A1 | 9/2009 | Mensinger et al. | |
| 2009/0240128 A1 | 9/2009 | Mensinger et al. | |
| 2009/0240193 A1 | 9/2009 | Mensinger et al. | |
| 2009/0242399 A1 | 10/2009 | Kamath et al. | |
| 2009/0242425 A1 | 10/2009 | Kamath et al. | |
| 2009/0247855 A1 | 10/2009 | Boock et al. | |
| 2009/0247856 A1 | 10/2009 | Boock et al. | |
| 2009/0287073 A1 | 11/2009 | Boock et al. | |
| 2009/0287074 A1 | 11/2009 | Shults et al. | |
| 2009/0299155 A1 | 12/2009 | Yang et al. | |
| 2009/0299156 A1 | 12/2009 | Simpson et al. | |
| 2009/0299162 A1 | 12/2009 | Brauker et al. | |
| 2009/0299276 A1 | 12/2009 | Brauker et al. | |

FOREIGN PATENT DOCUMENTS

| | | |
|---|---|---|
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-03/085372 | 10/2003 |
| WO | WO-2004/061420 | 7/2004 |
| WO | WO-2005/041766 | 5/2005 |
| WO | WO-2005/089103 | 9/2005 |
| WO | WO-2006/024671 | 3/2006 |
| WO | WO-2006/079114 | 7/2006 |
| WO | WO-2006/118947 | 11/2006 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/056638 | 5/2007 |
| WO | WO-2007/101223 | 9/2007 |
| WO | WO-2007/120363 | 10/2007 |
| WO | WO-2007/126444 | 11/2007 |
| WO | WO-2007/053832 | 12/2007 |
| WO | WO-2007/143225 | 12/2007 |
| WO | WO-2008/021913 | 2/2008 |
| WO | WO-2008/042760 | 4/2008 |
| WO | WO-2008/128210 | 10/2008 |
| WO | WO-2008/130896 | 10/2008 |
| WO | WO-2008/130897 | 10/2008 |
| WO | WO-2008/130898 | 10/2008 |
| WO | WO-2008/143943 | 11/2008 |
| WO | WO-2009/018058 | 2/2009 |
| WO | WO-2009/086216 | 7/2009 |
| WO | WO-2009/096992 | 8/2009 |
| WO | WO-2009/097594 | 8/2009 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Mediated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Johnson, P. C., "Peripheral Circulation", *John Wiley & Sons*, 1978, pp. 198.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain The Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectroscopy", *Clinical Chemistry*, vol. 45, No. 9, 1999, pp. 1651-1658.

McGarraugh, G., et al., "Physiological Influences on Off-Finger Glucose Testing", *Diabete Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

Wilson, G. S., et al., "Progress Toward the Development of an Implantable Sensor for Glucose", *Clinical Chemistry*, vol. 38, No. 9, 1992, pp. 1613-1617.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Jungheim, K., et al., "How Rapid Does Glucose Concentration Change in Daily Life of Patients with Type 1 Diabetes?", 2002, pp. 250.

McGarraugh, G., et al., "Glucose Measurements Using Blood Extracted from the Forearm and the Finger", *TheraSense, Inc.*, 2001, 16 Pages.

\* cited by examiner

ANALYTE SENSOR TRANSMITTER UNIT CONFIGURATION FOR A DATA MONITORING AND MANAGEMENT SYSTEM

BACKGROUND

Analyte monitoring systems including continuous glucose monitoring systems generally include an analyte sensor such as a subcutaneous analyte sensor, at least a portion of which is configured for fluid contact with biological fluid, for detecting analyte levels such as for example glucose or lactate levels, a transmitter (such as for example an RF transmitter) in communication with the sensor and configured to receive the sensor signals and to transmit them to a corresponding receiver unit by for example, using RF data transmission protocol. The receiver may be operatively coupled to a glucose monitor that performs glucose related calculations and data analysis.

The transmitter may be mounted or adhered to the skin of a patient and also in signal communication with the sensor. Generally, the sensor is configured to detect the analyte of the patient over a predetermined period of time, and the transmitter is configured to transmit the detected analyte information over the predetermined period of time for further analysis. To initially deploy the sensor so that the sensor contacts and electrodes are in fluid contact with the patient's analyte fluids, a separate deployment mechanism such as a sensor inserter or introducer is used. Moreover, a separate base component or mounting unit is provided on the skin of the patient so that the transmitter unit may be mounted thereon, and also, to establish signal communication between the transmitter unit and the analyte sensor.

As discussed above, the base component or mounting unit is generally adhered to the skin of the patient using an adhesive layer that is fixedly provided on the bottom surface of the base component or the mounting unit for the transmitter. To minimize data errors in the continuous or semi-continuous monitoring system, it is important to properly insert the sensor through the patient's skin and securely retain the sensor during the time that the sensor is configured to detect analyte levels. In addition to accurate positioning of the sensor through the skin of the patient, it is important to ensure that the appropriate electrode of the analyte sensor are in continuous and proper electrical connection or communication with the corresponding contact points or pads on the transmitter unit.

Additionally, for the period of continuous or semi-continuous monitoring which can include, for example, 3 days, 5 days or 7 days, it is important to have the transmitter unit securely mounted to the patient, and more importantly, in proper contact with the analyte sensor so as to minimize the potential errors in the monitored data.

In view of the foregoing, it would be desirable to have an approach to provide methods and system for accurate and simple ways in which to securely couple the analyte sensor with the transmitter unit so as to maintain continuous electrical connection therebetween. Moreover, it would be desirable to have methods and system for easy deployment of sensors and subsequent simple removal of the same in a time effective and straight forward manner.

SUMMARY OF THE INVENTION

In accordance with the various embodiment of the present invention, there is provided method and system for providing analyte sensor alignment and retention mechanism for improved connectivity with a transmitter unit for electrical connection, and further including transmitter unit contact pins with metal components to improve electrical conductivity with the analyte sensor in an analyte monitoring and management system.

These and other objects, features and advantages of the present invention will become more fully apparent from the following detailed description of the embodiments, the appended claims and the accompanying drawings.

DETAILED DESCRIPTION

Figure 1:
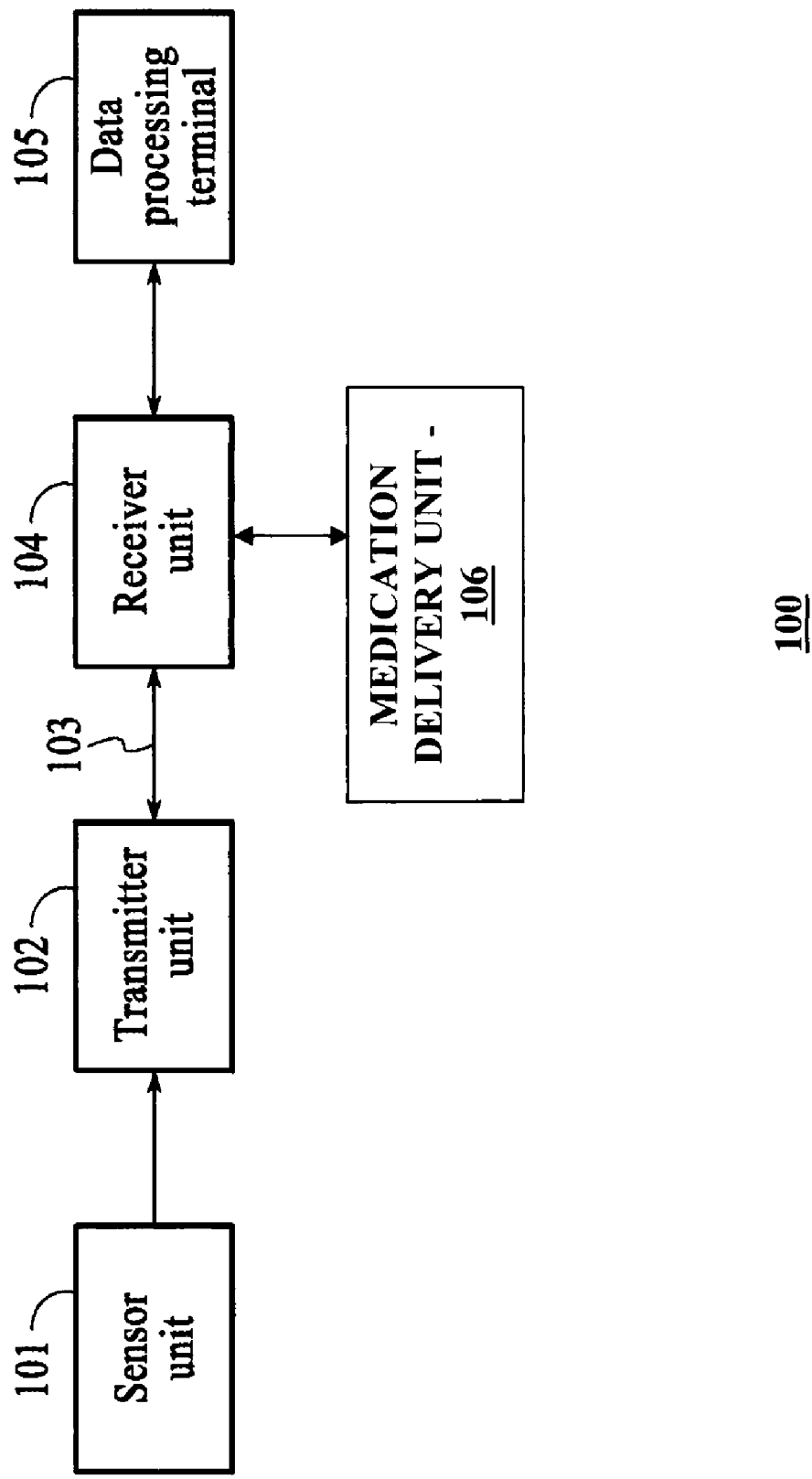
FIG. 1 is a block diagram illustrating a data monitoring and management system in accordance with one embodiment of the present invention.

FIG. 1 illustrates a data monitoring and management system such as, for example, an analyte monitoring and management system 100 in accordance with one embodiment of the present invention. In such embodiment, the glucose monitoring system 100 includes a sensor 101, a transmitter 102 coupled to the sensor 101, and a receiver 104 which is configured to communicate with the transmitter 102 via a communication link 103. The receiver 104 may be further configured to transmit data to a data processing terminal 105 for evaluating the data received by the receiver 104. In addition, as shown in the Figure, a medication delivery unit 106 maybe provided and operatively coupled to the receiver unit 104 and configured to receive one or more of data or commands directed to the control of the medical delivery unit 106 for delivering medication to a patient such as insulin.

Only one sensor 101, transmitter 102, communication link 103, receiver 104, data processing terminal 105, and medication delivery unit 106 are shown in the embodiment of the analyte monitoring and management system 100 illustrated in FIG. 1. However, it will be appreciated by one of ordinary skill in the art that the glucose monitoring system 100 may include one or more sensor 101, transmitter 102, communication link 103, receiver 104, and data processing terminal 105, where each receiver 104 is uniquely synchronized with a respective transmitter 102 to deliver medication through the medication delivery unit 106 such as an infusion pump. Moreover, within the scope of the present invention, the analyte monitoring and management system 100 may be a continuous monitoring and management system, or a semi-continuous or discrete monitoring and management system.

In one embodiment of the present invention, the sensor 101 is physically positioned on the body of a user whose glucose level is being monitored. The sensor 101 may be configured to continuously sample the glucose level of the user and convert the sampled analyte level into a corresponding data signal for transmission by the transmitter 102. In one embodiment, the transmitter 102 is mounted on the sensor 101 so that both devices are positioned on the user's body. The transmitter 102 performs data processing such as filtering and encoding on data signals, each of which corresponds to a sampled analyte level of the user, for transmission to the receiver 104 via the communication link 103.

In one embodiment, the analyte monitoring and management system 100 is configured as a one-way RF communication path from the transmitter 102 to the receiver 104. In such embodiment, the transmitter 102 transmits the sampled data signals received from the sensor 101 without acknowledgement from the receiver 104 that the transmitted sampled data signals have been received. For example, the transmitter 102 may be configured to transmit the encoded sampled data signals at a fixed rate (e.g., at one minute intervals) after the completion of the initial power on procedure. Likewise, the receiver 104 may be configured to detect such transmitted encoded sampled data signals at predetermined time intervals. Alternatively, the analyte monitoring and management system 100 may be configured with a bi-directional RF communication between the transmitter 102 and the receiver 104.

Additionally, in one aspect, the receiver 104 may include two sections. The first section is an analog interface section that is configured to communicate with the transmitter 102 via the communication link 103. In one embodiment, the analog interface section may include an RF receiver and an antenna for receiving and amplifying the data signals from the transmitter 102, which are thereafter, demodulated with a local oscillator and filtered through a band-pass filter. The second section of the receiver 104 is a data processing section which is configured to process the data signals received from the transmitter 102 such as by performing data decoding, error detection and correction, data clock generation, and data bit recovery.

In operation, upon completing the power-on procedure, the receiver 104 is configured to detect the presence of the transmitter 102 within its range based on, for example, the strength of the detected data signals received from the transmitter 102 or a predetermined transmitter identification information. Upon successful synchronization with the corresponding transmitter 102, the receiver 104 is configured to begin receiving from the transmitter 102 data signals corresponding to the user's detected glucose level. More specifically, the receiver 104 in one embodiment is configured to perform synchronized time hopping with the corresponding synchronized transmitter 102 via the communication link 103 to obtain the user's detected analyte level.

Referring again to FIG. 1, the data processing terminal 105 may include a desktop computer terminal, a data communication enabled kiosk, a laptop computer, a handheld computing device such as a personal digital assistant (PDAs), or a data communication enabled mobile telephone, and the like, each of which may be configured for data communication with the receiver via a wired or a wireless connection. Additionally, the data processing terminal 105 may further be connected to a data network (not shown) for storing, retrieving and updating data corresponding to the detected glucose level of the user. In addition, the data processing terminal 105 in one embodiment may include physician's terminal and/or a bedside terminal in a hospital environment, for example.

Moreover, the medication delivery unit 106 may include an infusion device such as an insulin infusion pump, which may be configured to administer insulin to patients, and which is configured to communicate with the receiver unit 104 for receiving, among others, the measured analyte level. Alternatively, the receiver unit 104 may be configured to integrate an infusion device therein so that the receiver unit 104 is configured to administer insulin therapy to patients, for example, for administering and modifying basal profiles, as well as for determining appropriate boluses for administration based on, among others, the detected glucose levels received from the transmitter 102. Referring again to FIG. 1, the medication delivery unit 106 may include, but not limited to an external infusion device such as an external insulin infusion pump, an implantable pump, a pen-type insulin injector device, a patch pump, an inhalable infusion device for nasal insulin delivery, or any other type of suitable delivery system.

Each of the transmitter unit 102, the receiver unit 104, the data processing unit 105, and the medication delivery unit 106 maybe configured to communicate with each other over a wireless data communication link similar to the communication link 103 such as, but not limited to RF communication link, Bluetooth communication link, infrared communication link, or any other type of suitable wireless communication connection between two or more electronic devices. The data communication link may also include wired cable connection such as, for example, but not limited to RS232 connection, USB connection, or serial cable connection.

Moreover, referring to FIG. 1, the analyte sensor unit 101 may include, but not limited to short term subcutaneous analyte sensors or transdermal analyte sensors, for example, which are configured to detect analyte levels of a patient over a predetermined time period.

Additional analytes that may be monitored, determined or detected by the analyte sensor unit 101 include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined.

Figure 2A:
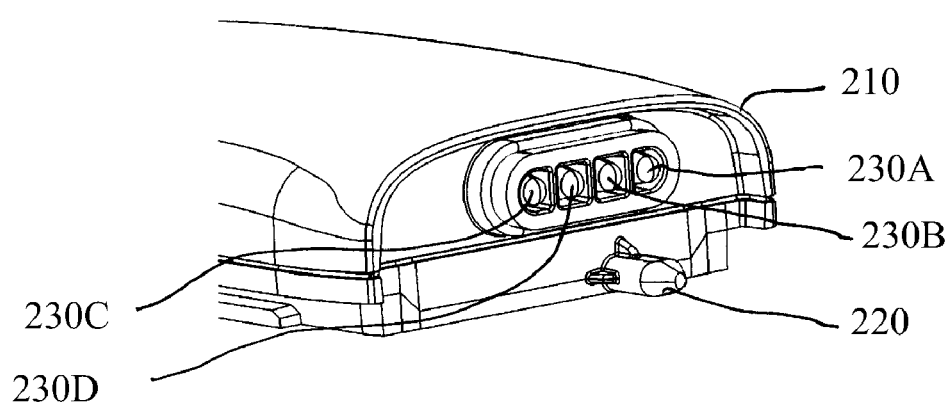
FIGS. 2A-2D illustrate various views of the analyte sensor alignment with a transmitter unit in accordance with one embodiment of the present invention.
Figure 2B:
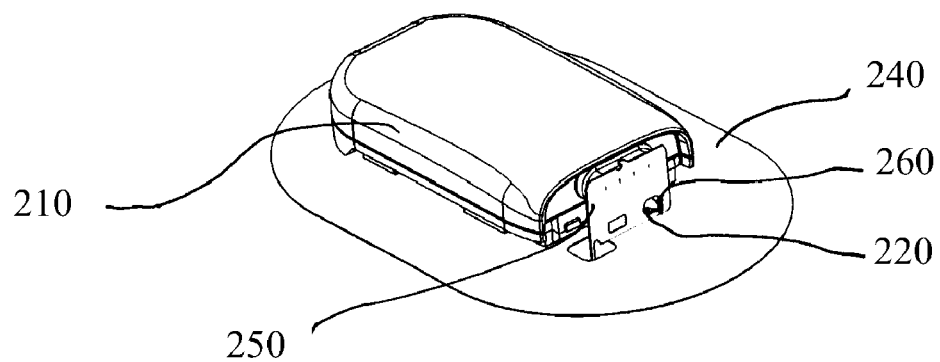

FIGS. 2A-2D illustrate various views of the analyte sensor alignment with a transmitter unit in accordance with one embodiment of the present invention. Referring to FIG. 2A, a transmitter unit 102 (FIG. 1) housing 210 is provided with a protrusion 220 substantially on the same side as the location of a plurality of transmitter contacts 230A, 230B, 230C, 230D, each of which are configured to couple to a respective segment of an analyte sensor 250 (FIG. 2B).

Figure 2C:
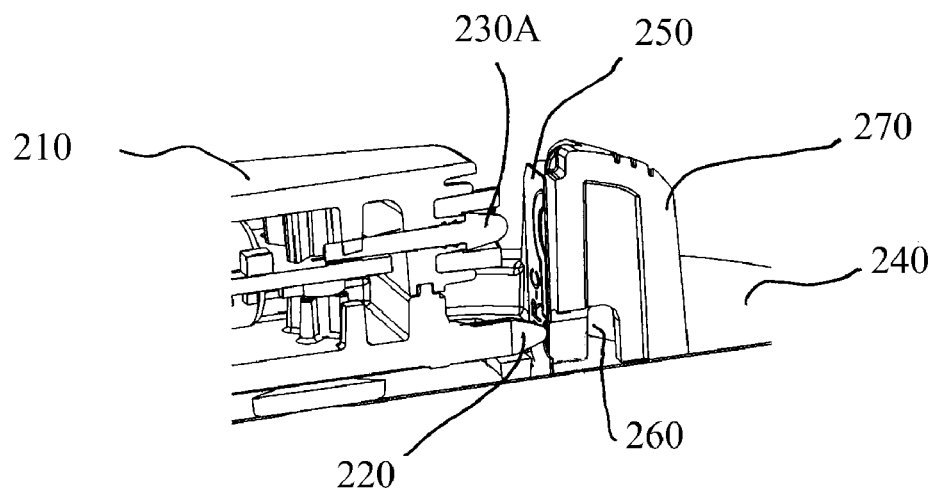
Figure 2D:
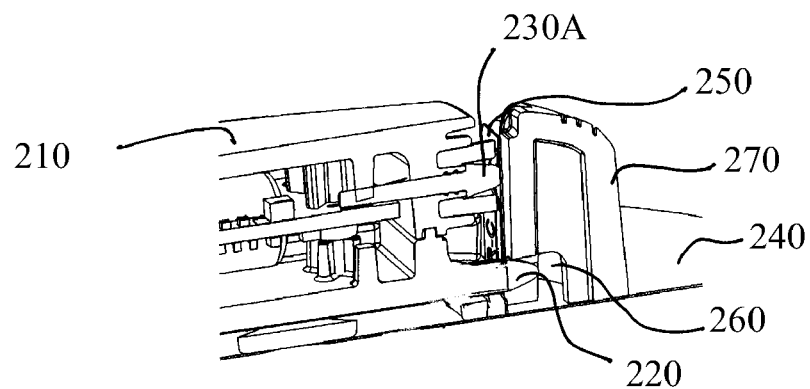

That is, when the transmitter unit housing 210 is positioned on an adhesive layer 240 for adhesion to a skin surface of a patient, the protrusion 220 of the transmitter unit housing 210 is configured to correspondingly mate with a notch or hole 260 on the surface of the analyte sensor 250 such that during the process of placing and guiding the transmitter unit on the adhesive layer 240 (and upon a transmitter mounting unit 270 (FIG. 2C)), it is possible to accurately position and align the transmitter contacts 230A, 230B, 230C, and 230D and to electrically couple to a respective one of the working electrode, the counter electrode, the reference electrode, and a guard trace, provided on the analyte sensor 250. Referring to FIGS. 2C and 2D, side cross sectional view of the transmitter contacts before and after alignment and engagement with the analyte sensor 250, respectively, are shown.

In the manner described above, in one embodiment of the present invention, there is provided a protrusion 220 on the transmitter unit housing 210 which is configured to mate with a notch or hole 260 on the analyte sensor 250 such that substantially accurate positioning and alignment of the analyte sensor 250 with respect to the transmitter unit 102 may be provided.

Figure 3A:
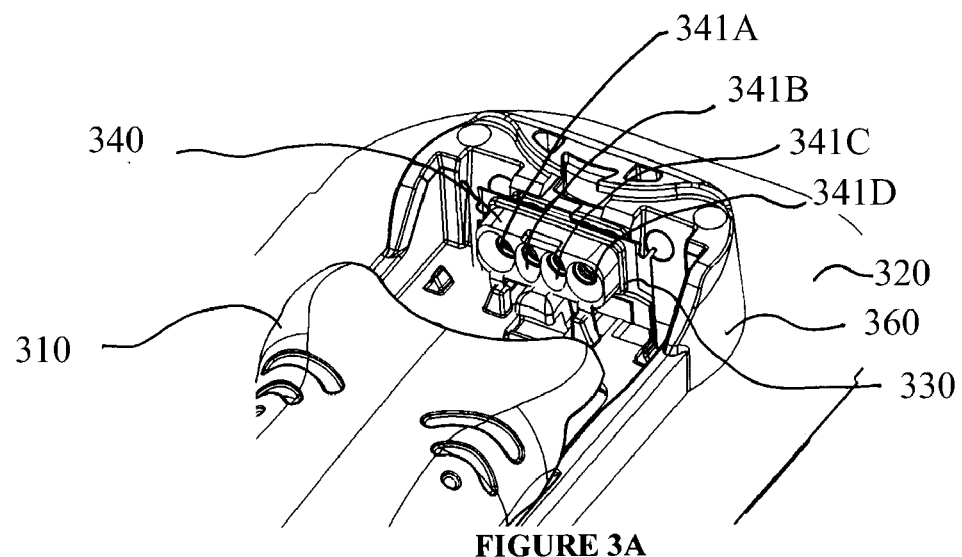
FIGS. 3A-3D illustrate various views of the analyte sensor alignment with a transmitter unit in accordance with another embodiment of the present invention.
Figure 3B:
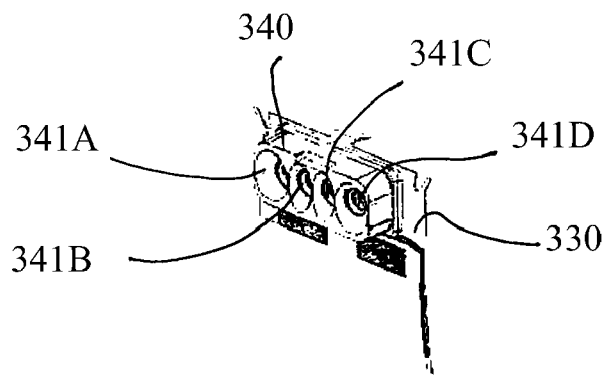
Figure 3C:
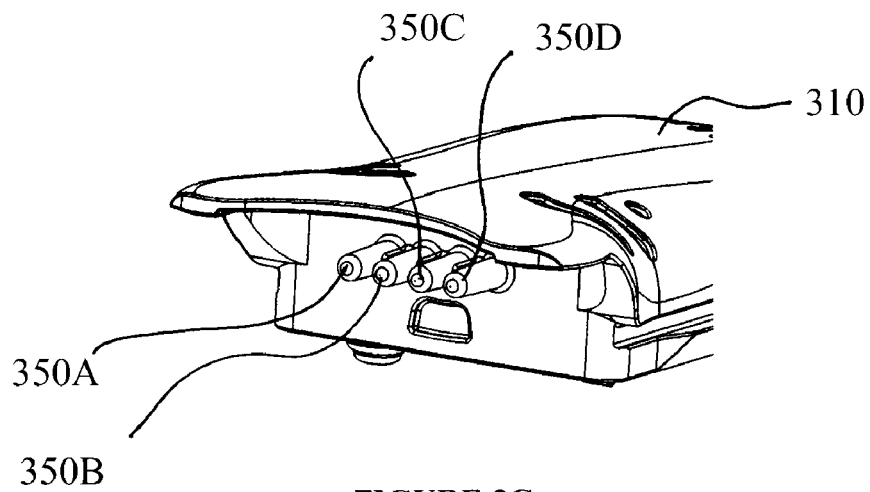

FIGS. 3A-3D illustrate various views of the analyte sensor alignment with a transmitter unit in accordance with another embodiment of the present invention. Referring to FIGS. 3A-3B, it can be seen that the analyte sensor 330 is provided with a seal 340 having a plurality of substantially circular lead-in segments 341A, 341B, 341C, 341D, each provided substantially respectively on one of the working electrode, counter electrode, reference electrode, and the guard trace of the analyte sensor 330. Moreover, referring to FIG. 3C, the electrical contact pins 350A, 350B, 350C, 350D on the transmitter unit housing 310 is each configured in substantially tapered manner extending outwards and away from the transmitter unit housing 310.

In this manner, in one embodiment of the present invention, when after analyte sensor 330 has been subcutaneously positioned through the skin of the patient, the transmitter unit housing 310 may be configured to mate with the transmitter mount unit 360 provided on the adhesive layer 320 such that the electrical contact pins 350A, 350B, 350C, 350D guided by the respective lead-in segments 341A, 341B, 341C, 341D on the sensor seal 340 such that the proper alignment of the sensor electrodes and guard trace are provided to the respective electrical contact pins 350A, 350B, 350C, 350D to establish electrical contacts with the same.

Figure 3D:
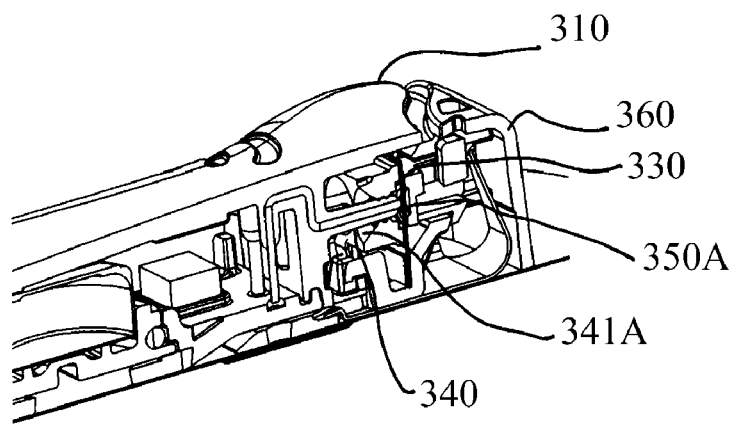

FIG. 3D illustrates a side cross sectional view of the electrical contact pins 350A, 350B, 350C, 350D on the transmitter unit 102 coupled to the respective lead-in segments 341A, 341B, 341C, 341D on the sensor seal 340 to establish electrical contact between the transmitter unit 102 (FIG. 1) and the analyte sensor 101. In one embodiment, the sensor seal 340 is provided on the analyte sensor 330 during the sensor manufacturing process, and as such, it is possible to achieve a high degree of accuracy in positioning the seal 340, and further, to obtain a substantially concentric lead-in segments 341A, 341B, 341C, 341D as shown, for example, in FIG. 3B, such that when the tip portion of the electrical contact pins 350A, 350B, 350C, 350D on the transmitter unit 102 are positioned within the concentric lead-in segments 341A, 341B, 341C, 341D, the proper alignment of the sensor contact pads or electrodes and guard trace with the respective electrical contact pins 350A, 350B, 350C, 350D on the transmitter unit 102 can be achieved.

Referring back to FIG. 3B, the seal 340 on the analyte sensor 330 may be provided during the manufacturing process of the sensor 330 and as such, pre-bonded to the sensor 330. In this manner, accurate alignment of the analyte sensor 330 with the transmitter unit 102 with a degree of tolerating potential misalignment of the electrical contact pins 350A, 350B, 350C, 350D on the transmitter unit 102 may be tolerated given the concentric shape of the lead-in segments 341A, 341B, 341C, 341D on the seal 340 of the analyte sensor 330.

Figure 4A:
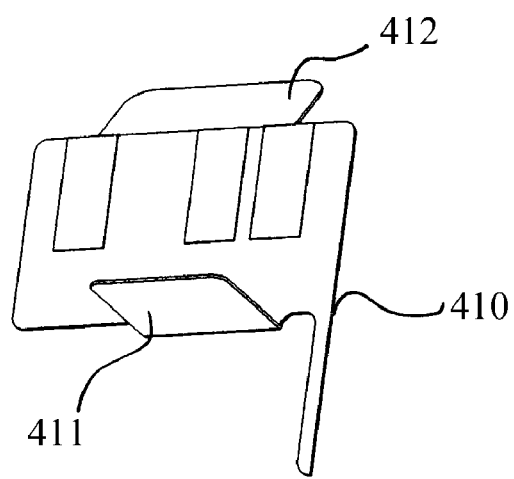
FIGS. 4A-4E illustrate various views of the analyte sensor latch configuration in accordance with one embodiment of the present invention.
Figure 4B:
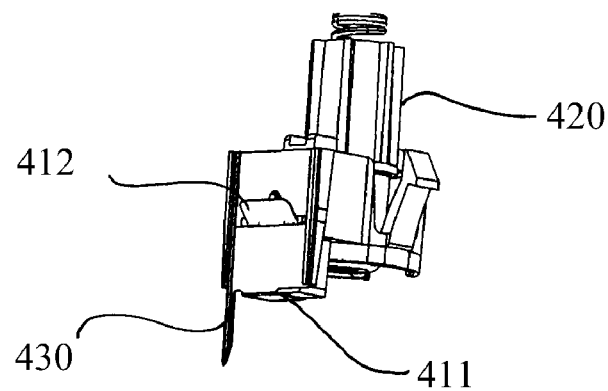

FIGS. 4A-4E illustrate various views of the analyte sensor latch configuration in accordance with one embodiment of the present invention. Referring to FIG. 4A, there is shown a sensor 410 having an upper flap portion 412 and a lower flap portion 411. The lower flap portion of the sensor 410 is configured in one embodiment to retain the sensor in proper position within a sharp or introducer 430 (FIG. 4B) of an insertion mechanism 420 (FIG. 4B) so as to minimize the potential sensor displacement prior to positioning the sensor in fluid contact with the patient's analytes using the insertion mechanism 420.

Figure 4C:
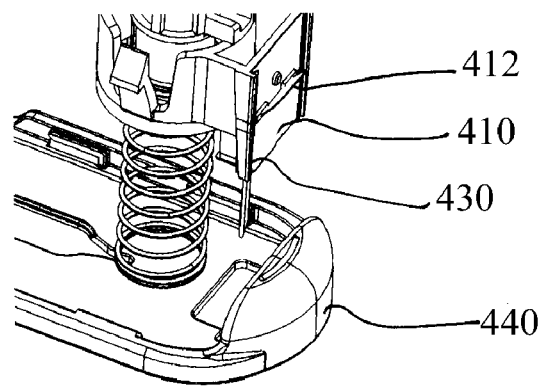
Figure 4D:
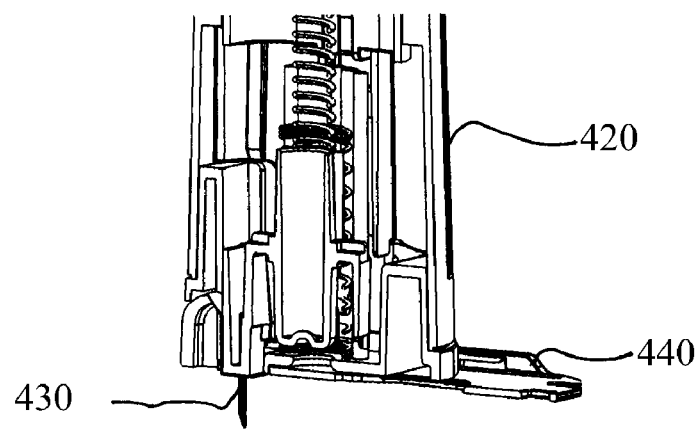
Figure 4E:
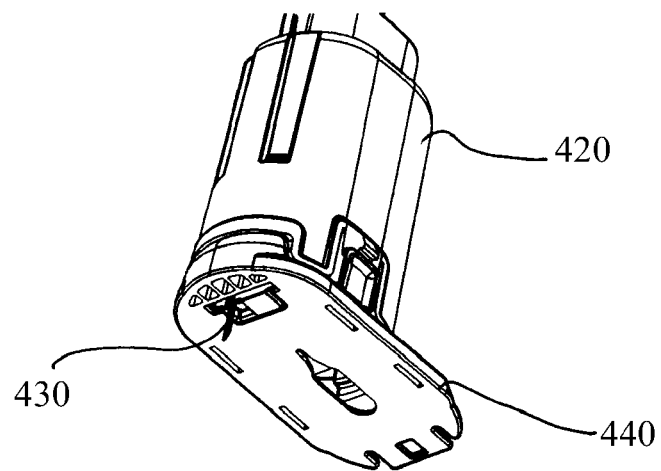

Referring back to FIG. 4A, the upper flap portion 412 of the sensor 410 is configured in one embodiment to facilitate the removal of the sensor 410 after its intended use (for example, 3 days, 5 days or 7 days), by providing an area which may be manually manipulated for removal from the inserted position in the patient. In one embodiment, the upper flap portion 412 and the lower flap portion 411 are extended in opposite direction relative to the body of the analyte sensor 410. This configuration further provides secure sensor positioning during the sensor insertion process such that the sensor movement when coupled to the introducer 430 is minimized. FIG. 4C illustrates the transmitter mount 440 in cooperation with the insertion mechanism 420 having the sensor 410 loaded in the introducer 430 before the sensor is placed in the patient. FIGS. 4D and 4E illustrate the insertion mechanism 420 coupled with the transmitter mount 440 after the insertion mechanism has deployed the introducer 430 so as to place at least a portion of the sensor 410 in fluid contact with the patient's analytes.

Figure 5A:
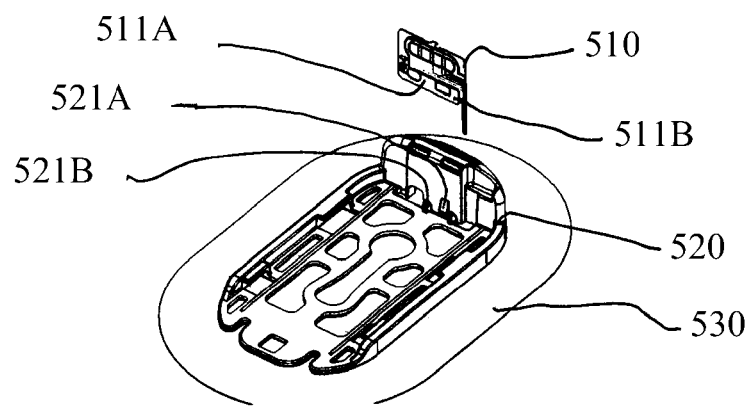
FIGS. 5A-5C illustrate various views of the analyte sensor latch configuration in accordance with another embodiment of the present invention.
Figure 5B:
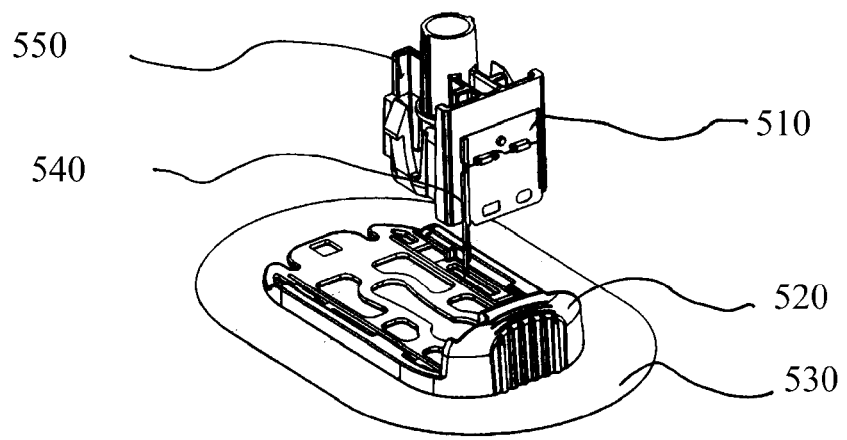
Figure 5C:
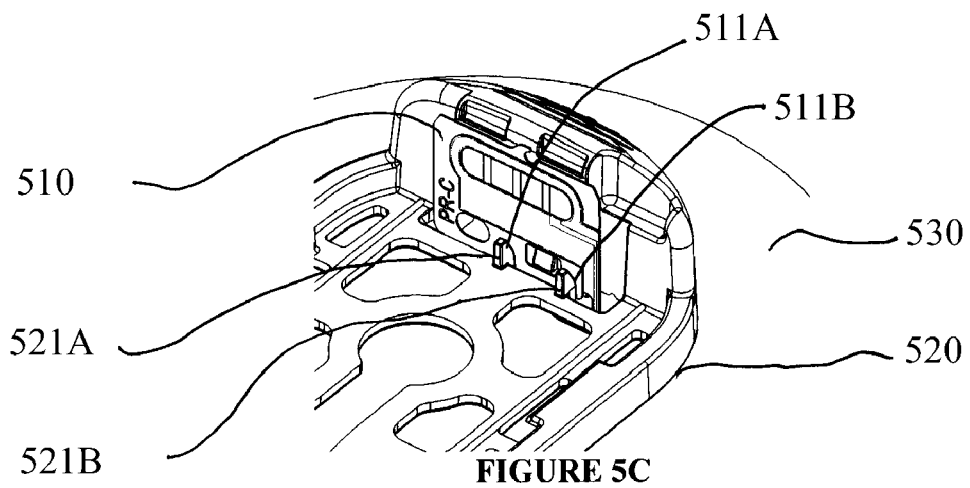

FIGS. 5A-5C illustrate various views of the analyte sensor latch configuration in accordance with another embodiment of the present invention. Referring to FIGS. 5A-5C, transmitter mount 520 is provided with a plurality of hooks (or barbs) 521A, 521B, each of which are configured to mate with a corresponding one of a plurality of open segments 511A, 511B on the sensor 510. During deployment of the sensor 510 for example, using an insertion mechanism 550 having an introducer 540 coupled to the sensor 510, the sensor 510 is positioned relative to the transmitter mount 520 such that the open segments 511A, 511B of the sensor 510 are coupled or latched with the respective hook/latch 521A, 521B on the transmitter mount 520, to securely retain the sensor 510 in position provide to the transmitter unit 102 being mounted on the transmitter mount 520 to couple to the sensor 210.

In one embodiment, the plurality of hooks/barbs 521A, 521B on the transmitter mount 520 are provided as molded plastic protrusions on the transmitter mount 520. Upon engaging with the respective open segments 511A, 511B on the sensor 510, it can be seen that the sensor 510 is retained substantially in a fixed position relative to the transmitter mount 520 (which is in turn, fixedly positioned on the patient's skin by the adhesive layer 530), so that proper alignment and coupling with the respective electrical contact pins on the transmitter unit 102 may be achieved.

Figure 6A:
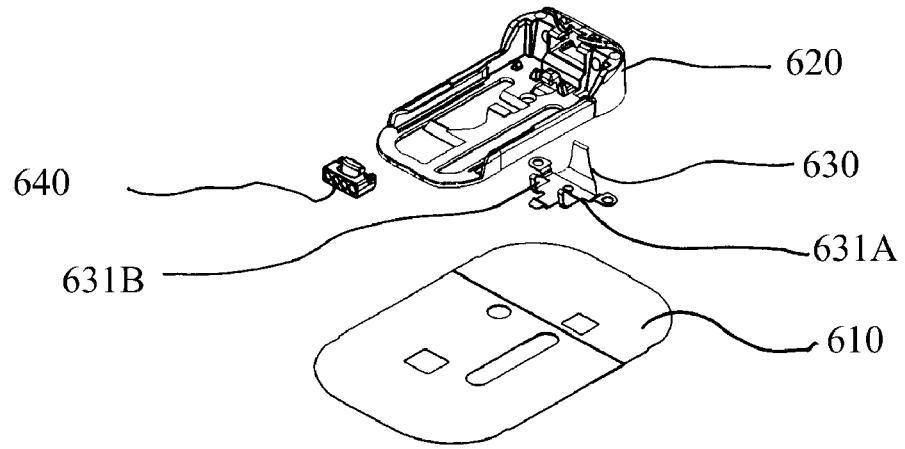
FIGS. 6A-6D illustrate various views of the analyte sensor latch configuration in accordance with yet another embodiment of the present invention.
Figure 6B:
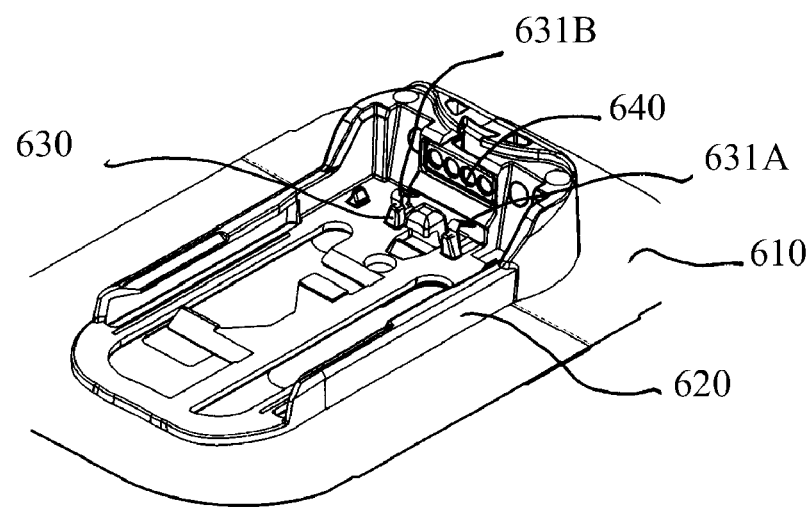

FIGS. 6A-6D illustrate various views of the analyte sensor latch configuration in accordance with yet another embodiment of the present invention. Referring to FIG. 6A illustrating a component view of the latch configuration, there is provided a transmitter mount 620, adhesive layer 610, a retaining segment 630 having a plurality of clip portions 631A, 631B, and a mounting segment 640. Referring to FIG. 6B, it can be seen that the retaining segment 630 is positioned on the transmitter mount 620 with the mounting segment provided thereon. Moreover, the transmitter mount is provided on the adhesive layer 620 which is in turn, placed on the patient's skin and adhered thereto for secure positioning.

Figure 6C:
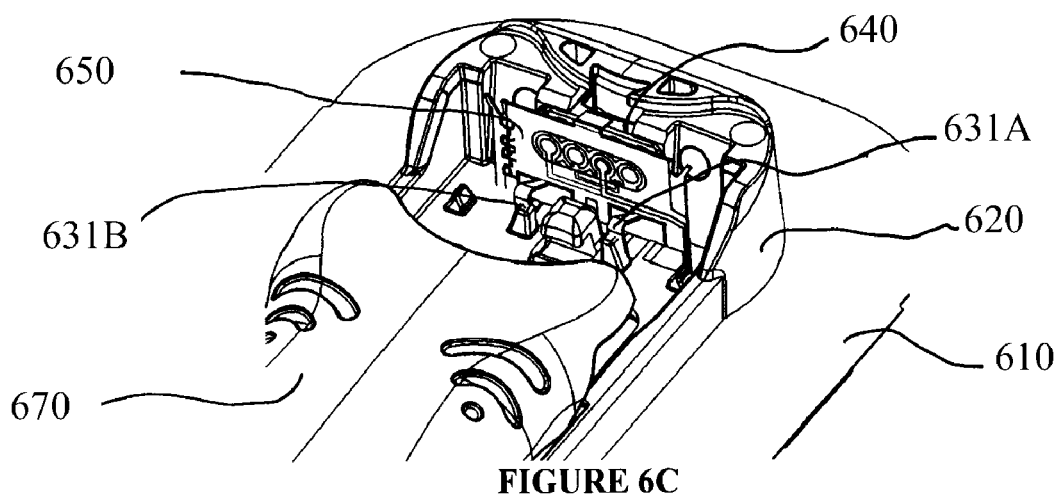
Figure 6D:
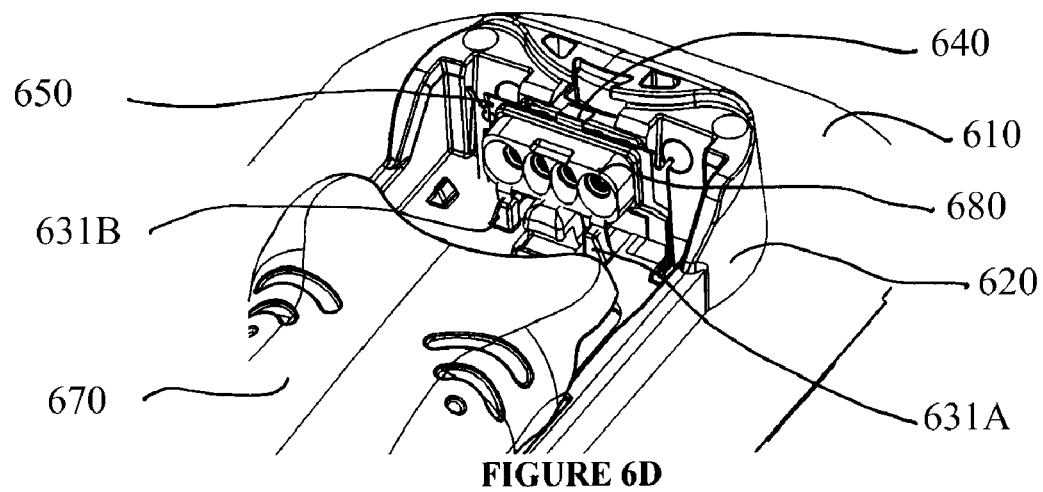
Figure 7A:
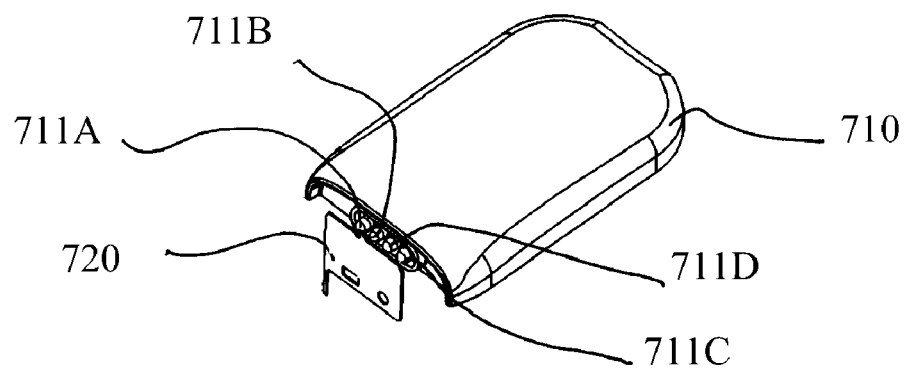
FIGS. 7A-7E illustrate a transmitter unit interconnect configuration in accordance with one embodiment of the present invention.
Figure 7B:
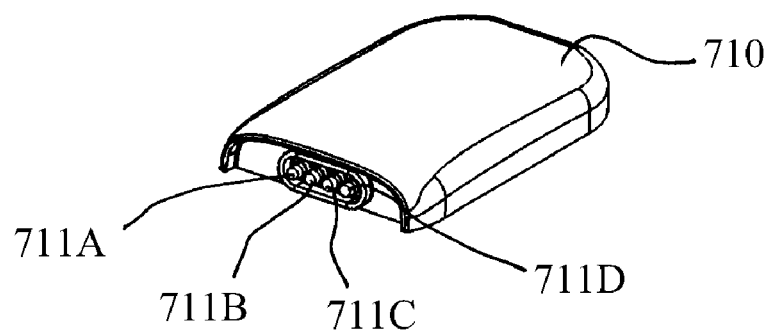
Figure 7C:
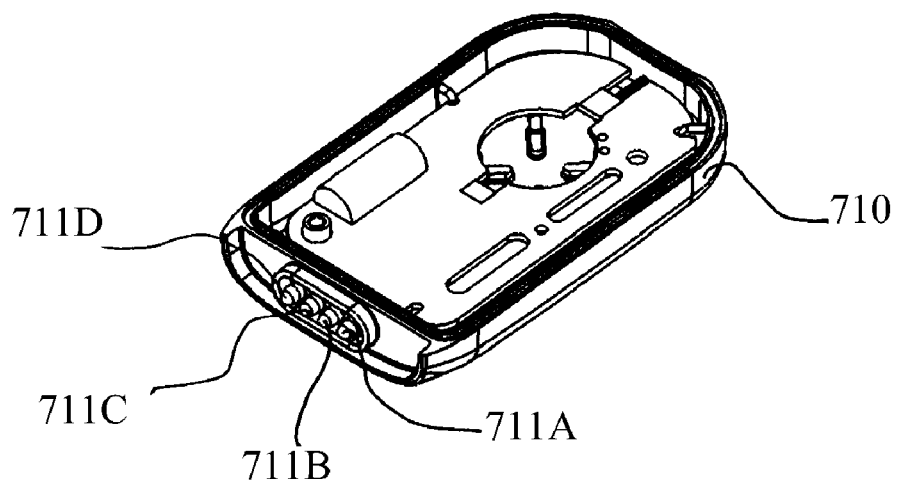
Figure 7D:
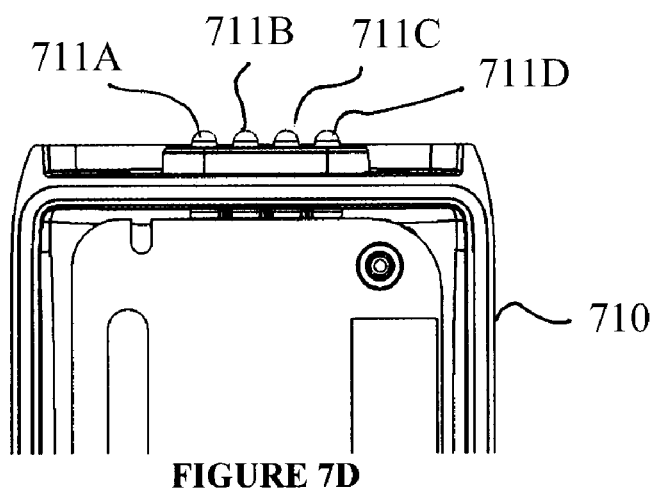
Figure 7E:
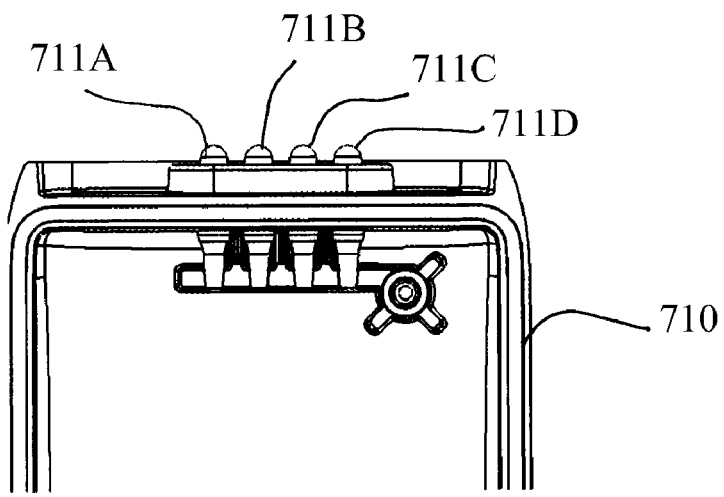

Referring to FIGS. 6C-6D, in one embodiment, the clip portions 631A, 631B of the retaining segment 630 are each spring biased and configured for spring loading the sensor 650 in the direction towards the electrical contact pins of the transmitter unit 102, thus facilitating the sensor (650)—transmitter (670) connection. Moreover, the clip portions 631A, 631B are further configured to provide a latch/locking mechanism of the subcutaneously positioned sensor 650 relative to the transmitter mount 620, such that the sensor 650 is held firmly in place.

In the manner described above, in accordance with the various embodiments of the present invention, there are provided different mechanism for sensor alignment relative to the transmitter electrical contact pins to effectively couple the sensor contacts (working, reference and counter electrodes and the guard trace), with the corresponding electrical contact pads or connections on the transmitter 102. Moreover, as further described above, in accordance with the various embodiments of the present invention, there are provided mechanism for sensor retention and secure positioning relative to the transmitter mount which is placed on the patient's skin such that the transmitter unit 102 may be easily and accurately guided to establish proper connection with the sensor unit 101.

FIGS. 7A-7E illustrate a transmitter unit interconnect configuration in accordance with one embodiment of the present invention. More specifically, FIGS. 7A-7E show various different perspectives and views of the transmitter unit housing 710 that includes a plurality of electrical contact pins 711A, 711B, 711C, 711D, each configured to establish electrical connection to a respective portion of the analyte sensor 720. As discussed below, each of the electrical contact pins 711A, 711B, 711C, 711D in one embodiment includes a polymer pin with a contact cap that provides improved electrical conductivity between the transmitter unit 102 and the sensor unit 101.

Figure 8A:
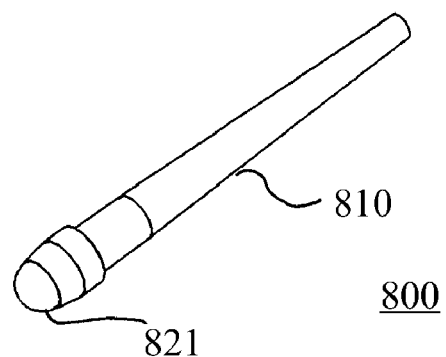
FIGS. 8A-8C illustrate a polymer pin with contact cap of the transmitter unit interconnect shown in FIGS. 7A-7E in one embodiment of the present invention.
Figure 8B:
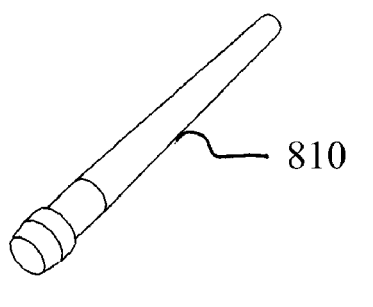
Figure 8C:
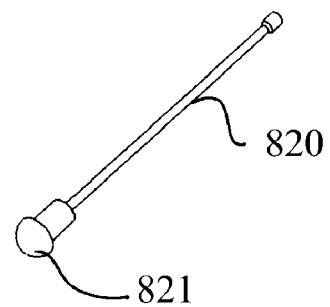

FIGS. 8A-8C illustrate a polymer pin with contact cap of the transmitter unit interconnect shown in FIGS. 7A-7E in one embodiment of the present invention. As shown in FIGS. 8A-8C, contact pin 800 includes an outer body portion 810 and an inner contact portion 820 with an end segment 821. In one embodiment, the inner contact portion 820 is configured to substantially entirely be positioned within the outer body portion 810 (as shown in FIG. 8A), except for the end segment 821 of the inner contact portion 820 extending out of one end of the outer body portion 810.

In one embodiment, the outer body portion 810 maybe injection molded using a silicone based, carbon loaded (impregnated, for example) soft polymer material. Furthermore, the end segment 821 and the inner contact portion 820 comprise a metal such as for example, Beryllium copper (BeCu), Nickel Silver, Phosphor Bronze Brass, Rhodium or gold plated to provide improved electrical conductivity. More specifically, the inner contact portion 820 placed within the outer body portion 810 may comprise a light gauge wire (such as 30 g), and may be insert molded into the outer body portion 810.

In this manner, the contact pin 800 in one embodiment includes a carbon loaded, silicone based, injection molded soft polymer pin with a metal cap or end segment 821 which is shaped and positioned to cover substantially a large portion of the contact area where the sensor contact is to occur. Moreover, the metal inner contact portion 820 extending the length of the outer body portion 810 of the contact pin 800 further improves electrical conductivity. Moreover, a metal end segment 821 provides additional resistance to wear over a prolonged use based on repeated contact with other surfaces (for example, sensor surfaces).

Accordingly, in one aspect of the present invention, the transmitter unit 102 may be provided with a plurality of contact pins 800 that have a large metal sensor contact surface to increase the electrical conductivity with the sensor. In addition, the metal contact surface may provide improved resistance to abrasion, wear and damage to the end segment 821 of the contact pin 800. In addition, the contact pin 800 configuration described above also provides flexibility, desired compliance and self-sealing capability, and further, may be press fit into the transmitter housing. Further, the contact pins 800 may additionally be chemically resistant, substantially water proof, and thus improve the transmitter unit 102 interconnect assembly life.

Accordingly, an apparatus for providing alignment in one embodiment of the present invention includes a sensor having a hole thereon, and a transmitter housing including a protrusion at a first end, the protrusion configured to substantially engage with the hole of the sensor such that the transmitter is in electrical contact with the sensor.

An apparatus for providing alignment in accordance with another embodiment of the present invention includes a sensor including a plurality of conductive pads, and a transmitter housing including a plurality of electrical contacts, each of the electrical contacts configured to substantially align with a respective one of the plurality of the conductive pads.

The apparatus may further include a seal segment adhered to the sensor, where the seal segment includes a plurality of radial seal holes disposed on the seal segment, and further, where each of the radial holes may be configured to receive a respective one of the plurality of electrical contacts.

In another aspect, each of the electrical contacts may be substantially tapered.

Moreover, the transmitter electrical contacts may be configured to self-align with a respective one of the conductive pads of the sensor when the transmitter is coupled to the sensor.

An apparatus for providing a sensor connection in a data monitoring system in accordance with yet another embodiment of the present invention includes a sensor having a plurality of conductive pads, and a transmitter housing, the housing including a plurality of electrical contacts, each of the contacts configured to substantially contact the respective one of the sensor conductive pads, where each of the plurality of electrical contacts include conductive polymer.

The electrical contacts in one embodiment may be silicon doped with carbon.

Moreover, the electrical contacts maybe substantially conical shaped.

In another aspect, each of the electrical contacts may include a metal component disposed therein, wherein at least a first end of each of the electrical contacts is configured to substantially contact the respective one of the sensor conductive pads.

The metal component may include one of gold or beryllium copper.

An apparatus for providing a sensor connection in a data monitoring system in still another embodiment of the present invention includes a sensor having a plurality of conductive pads, a transmitter mount having a spring biased mechanism, and a transmitter housing, the housing including a plurality of electrical contacts, where each of the plurality of electrical contacts of the transmitter is configured to substantially contact the respective one of the sensor conductive pads by the spring biased mechanism of the transmitter housing.

In yet another aspect, the spring biased mechanism of the transmitter mount may include a tapered cantilever beam disposed on the transmitter mount.

An apparatus for positioning a sensor in a data monitoring system in yet still another embodiment of the present invention may include a sensor having a cutout portion, and a transmitter mount having a latch mechanism, the transmitter mount configured to couple to the sensor by the latch mechanism engaging the cutout portion of the sensor.

An apparatus for positioning a sensor in a data monitoring system in yet still a further embodiment of the present invention may include a sensor, and a transmitter mount, the transmitter including a latch mechanism, the latch mechanism configured to engage with the sensor for substantially permanently positioning the sensor relative to the transmitter.

Further, the latch mechanism may in one embodiment include a metal clip.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. An apparatus for providing a sensor connection in a data monitoring system, comprising:
   a sensor having a plurality of conductive pads;
   a transmitter mount including a retaining segment, the retaining segment having a spring biased mechanism, wherein the spring biased mechanism includes a tapered protrusion disposed on the retaining segment; and
   a transmitter housing, the housing including a plurality of electrical contacts;
      wherein each of the plurality of electrical contacts of the transmitter housing is configured to substantially contact a respective one of the sensor conductive pads by the spring biased mechanism of the retaining segment when the transmitter housing is mated with the transmitter mount, and each of the plurality of electrical contacts includes a portion which is physically contacted with the corresponding one of the plurality of conductive pads of the sensor; and
      wherein the transmitter mount includes an opening to detachably couple to the transmitter housing when the sensor is connected to the transmitter housing.

2. The apparatus of claim 1 wherein each of the electrical contacts is substantially tapered.

3. The apparatus of claim 1 wherein the transmitter housing electrical contacts are configured to self-align with a respective one of the conductive pads of the sensor when the transmitter housing is coupled to the sensor.

4. The apparatus of claim 1 wherein the sensor includes a planar surface, and the plurality of conductive pads are provided on the planar surface.

5. The apparatus of claim 4 wherein each of the transmitter housing electrical contacts is configured to substantially contact the respective one of the sensor conductive pads on said planar surface of the sensor.

6. The apparatus of claim 1 wherein each of the plurality of electrical contacts includes a conductive polymer.

7. The apparatus of claim 1 wherein the transmitter housing electrical contacts are silicon doped with carbon.

8. The apparatus of claim 1 wherein the transmitter housing electrical contacts are substantially conical shaped.

9. The apparatus of claim 1 wherein each of the transmitter housing electrical contacts includes a metal component disposed therein, wherein at least a first end of each of the electrical contacts is configured to substantially contact the respective one of the sensor conductive pads.

10. The apparatus of claim 9 wherein the metal component includes one of gold or beryllium copper.

11. The apparatus of claim 1 wherein the sensor includes a cutout portion, and further, wherein the transmitter mount includes a latch mechanism to couple to the sensor by engaging the cutout portion of the sensor.

12. The apparatus of claim 11 wherein the latch mechanism is configured to engage with the sensor for substantially permanently positioning the sensor relative to the transmitter mount.

13. The apparatus of claim 11 wherein the latch mechanism includes a metal clip.

14. The apparatus of claim 1 wherein the transmitter mount is configured for positioning on a skin surface such that the transmitter mount is positioned between the skin surface and the transmitter housing.

15. An apparatus for providing a sensor connection in a data monitoring system, comprising:
   a sensor having a plurality of conductive pads;
   a transmitter mount including a retaining segment, the retaining segment having a spring biased mechanism;
   a transmitter housing, the housing including a plurality of electrical contacts;
      wherein each of the plurality of electrical contacts of the transmitter housing is configured to substantially contact a respective one of the sensor conductive pads by the spring biased mechanism of the retaining segment when the transmitter housing is mated with the transmitter mount, and each of the plurality of electrical contacts includes a portion which is physically contacted with the corresponding one of the plurality of conductive pads of the sensor; and
      wherein the transmitter mount includes an opening to detachably couple to the transmitter housing when the sensor is connected to the transmitter housing; and
   a seal segment adhered to the sensor, wherein the seal segment includes a plurality of radial seal holes disposed on the seal segment.

16. The apparatus of claim 15 wherein each of the radial holes is configured to receive a respective one of the plurality of electrical contacts.

17. The apparatus of claim 15 wherein each of the plurality of electrical contacts includes a conductive polymer.

18. The apparatus of claim 15 wherein each of the transmitter housing electrical contacts includes a metal component disposed therein, wherein at least a first end of each of the electrical contacts is configured to substantially contact the respective one of the sensor conductive pads.

19. The apparatus of claim 18 wherein the metal component includes one of gold or beryllium copper.

20. The apparatus of claim 15 wherein the sensor includes a planar surface, and the plurality of conductive pads are provided on the planar surface.

* * * * *